(12) United States Patent
Malkowski

(10) Patent No.: US 8,685,003 B2
(45) Date of Patent: Apr. 1, 2014

(54) DUAL CABLE TRIANGULATION MECHANISM

(75) Inventor: Jaroslaw T. Malkowski, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/412,115

(22) Filed: Mar. 5, 2012

(65) Prior Publication Data

US 2012/0253327 A1  Oct. 4, 2012

Related U.S. Application Data

(60) Provisional application No. 61/468,863, filed on Mar. 29, 2011.

(51) Int. Cl.
*A61B 17/00* (2006.01)

(52) U.S. Cl.
USPC .............. 606/1; 606/205; 606/206; 606/207; 606/208

(58) Field of Classification Search
USPC ................. 606/1, 205–208; 600/210
See application file for complete search history.

(56) References Cited

U.S. PATENT DOCUMENTS

| | | | |
|---|---|---|---|
| 4,066,071 A * | 1/1978 | Nagel | 600/102 |
| 4,898,577 A | 2/1990 | Badger et al. | |
| 4,998,916 A | 3/1991 | Hammerslag et al. | |
| 5,007,434 A | 4/1991 | Doyle et al. | |
| 5,306,245 A | 4/1994 | Heaven | |
| 5,441,483 A | 8/1995 | Avitall | |
| 5,472,017 A | 12/1995 | Kovalcheck | |
| 5,507,725 A | 4/1996 | Savage et al. | |
| 5,511,564 A * | 4/1996 | Wilk | 128/898 |
| 5,743,880 A | 4/1998 | Hlavka | |
| 6,068,621 A | 5/2000 | Balceta et al. | |
| 6,554,794 B1 | 4/2003 | Mueller et al. | |
| 7,250,027 B2 | 7/2007 | Barry | |
| 7,527,620 B2 | 5/2009 | Long et al. | |
| 7,637,903 B2 | 12/2009 | Lentz et al. | |
| 7,682,319 B2 | 3/2010 | Martin et al. | |
| 7,758,564 B2 | 7/2010 | Long et al. | |
| 7,763,012 B2 | 7/2010 | Petrick et al. | |
| 7,811,277 B2 | 10/2010 | Boulais | |
| 2003/0149422 A1 | 8/2003 | Muller | |
| 2004/0054322 A1 | 3/2004 | Vargas | |
| 2005/0014995 A1 | 1/2005 | Amundson et al. | |
| 2007/0049966 A1* | 3/2007 | Bonadio et al. | 606/206 |
| 2007/0208312 A1 | 9/2007 | Norton et al. | |
| 2007/0270679 A1 | 11/2007 | Nguyen et al. | |
| 2008/0009747 A1 | 1/2008 | Saadat et al. | |
| 2008/0097391 A1 | 4/2008 | Feinberg et al. | |
| 2008/0188869 A1 | 8/2008 | Weitzner et al. | |
| 2008/0281293 A1 | 11/2008 | Peh et al. | |
| 2009/0005755 A1 | 1/2009 | Keith et al. | |

(Continued)

FOREIGN PATENT DOCUMENTS

WO  WO 2010136274 A1 *  12/2010

*Primary Examiner* — Bill Thomson
*Assistant Examiner* — Boniface N Nganga

(57) ABSTRACT

A surgical system is adapted and configured for use in a minimally invasive surgical procedure. The surgical system includes a surgical instrument that is operatively coupled to a seal anchor member for accessing an underlying body cavity and manipulating a target tissue within the body cavity. The surgical instrument includes a plurality of arms that are triangulatable with respect to each other and the target tissue.

16 Claims, 12 Drawing Sheets

(56) References Cited

U.S. PATENT DOCUMENTS

| | | |
|---|---|---|
| 2009/0024086 A1 | 1/2009 | Zhang et al. |
| 2009/0043299 A1 | 2/2009 | Racz |
| 2009/0157076 A1 | 6/2009 | Athas et al. |
| 2009/0192495 A1 | 7/2009 | Ostrovsky et al. |
| 2009/0198179 A1 | 8/2009 | Abbate et al. |
| 2010/0004633 A1 | 1/2010 | Rothe et al. |
| 2011/0011410 A1* | 1/2011 | Desai et al. .................. 128/898 |
| 2012/0116362 A1* | 5/2012 | Kieturakis ....................... 606/1 |

* cited by examiner

DUAL CABLE TRIANGULATION MECHANISM

CROSS-REFERENCE TO RELATED APPLICATIONS

The present application claims priority to, and the benefit of, U.S. Provisional Patent Application Ser. No. 61/468,863, filed Mar. 29, 2011, the entire contents of which are hereby incorporated by reference.

BACKGROUND

1. Technical Field

The present disclosure relates generally to a surgical device for use in a minimally invasive surgical procedure. More particularly, the present disclosure relates to an articulating surgical instrument having at least a first and a second segment that are separately movable.

2. Background of Related Art

A minimally invasive surgical procedure is one in which a surgeon enters a patient's body through one or more small opening in the patient's skin or a naturally occurring opening (e.g., mouth, anus, or vagina). As compared with traditional open surgeries, minimally invasive surgical procedures have several advantages and disadvantages. Minimally invasive surgeries include arthroscopic, endoscopic, laparoscopic, and thoracic surgeries. Advantages of minimally invasive surgical procedures over traditional open surgeries include reduced trauma and recovery time for patients.

However, some disadvantages include a lack of direct visualization of the surgical site and reduced dexterity of instruments, as compared to traditional open surgeries. In particular, the simultaneous manipulation of the viewing instrument and surgical instruments that are inserted into the opening may be complicated. One complication arises from the difficulty in visualizing surgical instruments on a monitor that is operably coupled to the viewing instrument.

One surgical technique used to increase the ability of the surgeon to visualize and access critical anatomy is triangulation. Triangulation is a principle in which the surgical instrument and the viewing instrument are held so that their tips form the apex of an imaginary triangle. In particular, the viewing instruments may be in the middle of the surgical field, and the surgical instruments may be angled with respect to the viewing instrument as to form an imaginary triangle.

In minimally invasive surgical procedures through a single incision, straight and rigid surgical instruments are inserted through a single incision. To control the instruments, a surgeon often crosses his hands. The lack of triangulation makes visualization and access of critical anatomy potentially difficult. Furthermore, it is desirable to coordinate the positions of end effectors of the surgical instruments.

Consequently, a continuing need exists for improved minimally invasive surgical devices.

SUMMARY

Disclosed herein is a surgical system for use during a minimally invasive surgical procedure.

The surgical system includes a seal anchor member and a surgical instrument including arms that are triangulatable with respect to one another. The surgical instrument is configured and adapted to be operatively coupled with the seal anchor member that can be placed in an incision or in a naturally occurring bodily orifice (e.g., mouth, anus, or vagina).

The seal anchor member includes two or more longitudinally extending ports. Each port is configured and adapted to receive, in a sealed relation, one of the arms of the surgical instrument. The surgical instrument includes arms including at least first and second segments that are independently actuatable with respect to one another. In an embodiment, the surgical instrument includes a first arm and a second arm, each arm including a first and a second segment that are individually and selectively positioned and oriented. Movement of the first and second arms may be choreographed or synchronized with respect to one another.

Each of the first and second segments includes a plurality of rings and an annular member that is operably coupled to a pair of cables. The pairs of cables are individually and independently actuatable. In an embodiment, the first and second annular member members have different dimensions. In a further embodiment, a collar is disposed about at least one of the first and second annular member members and is translatable along a longitudinal axis of the at least one of the first and second annular member members. Gears may be used to facilitate synchronized movement of the arms.

A method of performing surgery is also disclosed. In an embodiment, a surgical system is provided. The surgical system includes a seal anchor member including one or more longitudinally extending ports. The surgical instrument is configured and adapted to be placed within the one or more longitudinally extending ports. The surgical instrument includes a first arm and a second arm. Each arm includes a first segment and a second segment. The first segment includes a plurality of rings and a first annular member. The second segment includes a plurality of rings and a second annular member. The first and the second seconds are independently actuatable. A surgeon places the surgical system within a tissue tract defined within a tissue of the patient. The arms are actuated to effect triangulating of the arms with respect to one another and a target location within the surgical site. After completing the desired procedure, the surgical system is removed from the tissue tract.

These and other features of the current disclosure will be explained in greater detail in the following detailed description of the various embodiments.

BRIEF DESCRIPTION OF THE DRAWINGS

Various embodiments of the present disclosure are described hereinbelow with reference to the drawings, wherein.

DETAILED DESCRIPTION OF THE EMBODIMENTS

Figure 1:
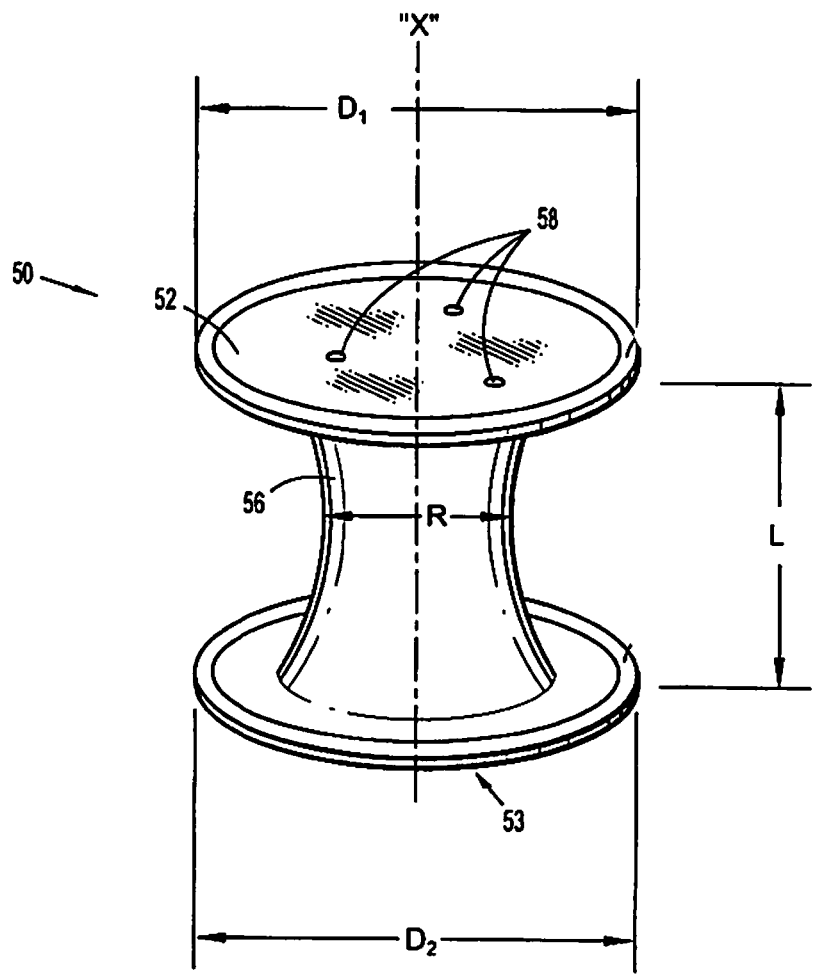
FIG. 1 is a front perspective view of a seal anchor member shown positioned relative to tissue.
Figure 1:
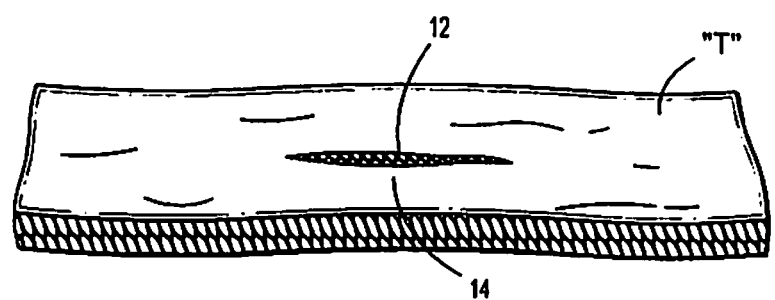

Particular embodiments of the present disclosure will be described herein with reference to the accompanying drawings. As shown in the drawings and as described throughout the following descriptions, and as is traditional when referring to relative positioning on an object, the term "proximal" will refer to the end of the apparatus that is closest to the clinician during use, and the term "distal" will refer to the end that is farthest from the clinician during use.

With reference to FIG. 1, a seal anchor member 50 for use in a minimally invasive surgical procedure will now be described. The seal anchor member 50 defines a longitudinal axis "X" and has respective trailing (or proximal) and leading (or distal) ends 52, 53 and an intermediate portion 56 disposed between the trailing and leading ends 52, 53. Seal anchor 50 includes one or more ports 58 that extend longitudinally between trailing and leading ends 52, 53, respectively, and through seal anchor member 50. The trailing end 52 defines a first diameter $D_1$, and the leading end 53 defines a second diameter $D_2$. The intermediate portion 56 defines a radial dimension R. The radial dimension R may be less than the first and second diameters $D_1$, $D_2$ and may vary along length L of the seal anchor member 50 to define a substantially hour-glass configuration. The seal anchor member 50 is insertable within tissue tract 12 defined between tissue surfaces 14 of tissue "T". The hour-glass configuration of the intermediate section 56 may facilitate anchoring of the seal anchor member 50 within the tissue tract 12. The seal anchor member 50 is configured and adapted to establish a sealing relation with the tissue "T". An example of such a seal anchor member 50 is illustrated in commonly assigned U.S. Pat. Pub. 2009/0093752.

Embodiments of surgical systems 150, 250, 350, 450, 550 include surgical instruments 100-500, respectively, will now be described with reference to FIGS. 2-13. Each of the surgical instruments 100-500 include at least two arms that are configured and adapted to triangulate with respect to one another, and are configured and adapted placed within ports of a seal anchor member, e.g., seal anchor member 50. Each of the surgical instruments 100-500 include at least two arms 102, 202, 302, 402, 502 that may be configured and adapted for substantially synchronized movement with respect to one another.

Figure 2:
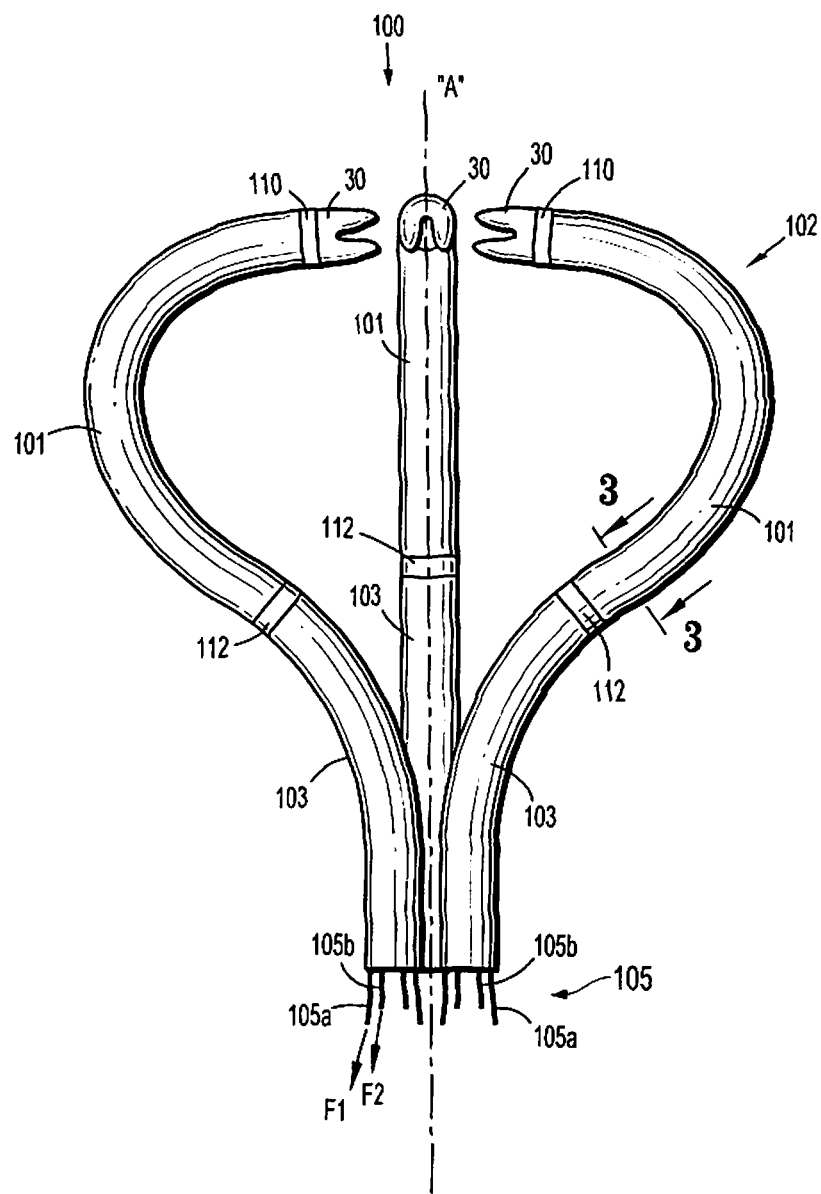
FIG. 2 is a perspective view of a surgical instrument in accordance with the present disclosure and shown in a triangulated condition.
Figure 2A:
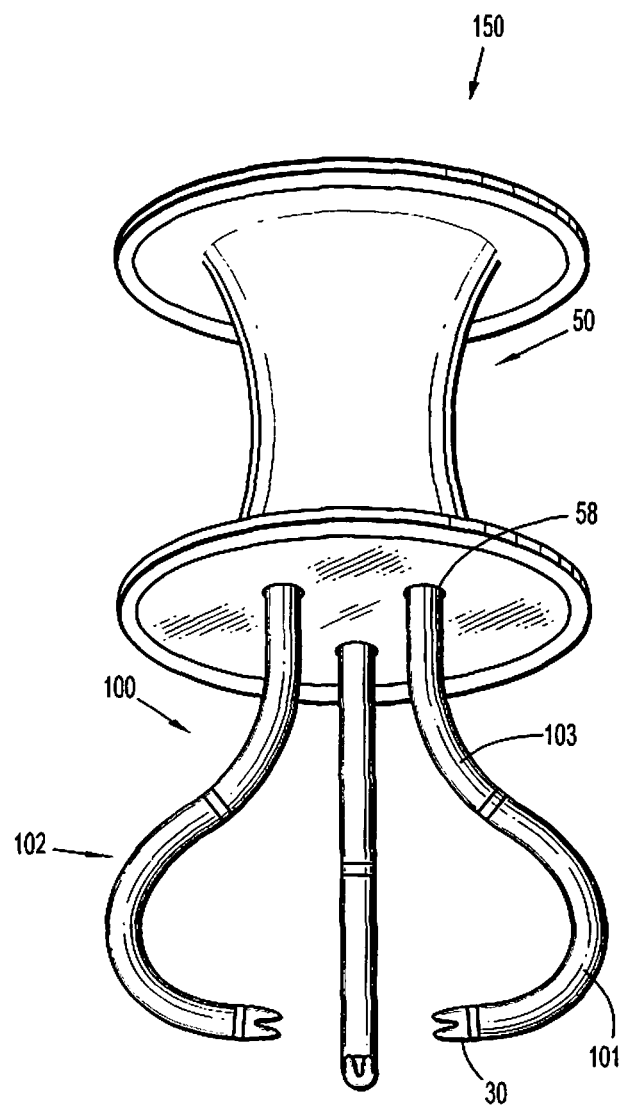
FIG. 2A is a bottom perspective view of a surgical system including the surgical instrument of FIG. 2 shown operatively coupled to the seal anchor member of FIG. 1.

Surgical instrument 100 will now be described with reference to FIGS. 2-4. As shown in FIG. 2, the surgical instrument 100 includes a plurality of arms 102. As shown in FIG. 2A, a surgical system 150 includes the surgical instrument 100. The surgical instrument 100 is operatively coupled to the seal anchor member 50.

Each arm 102 of the surgical instrument 100 is configured and adapted to be placed within port 58 of the seal anchor member 50. As shown in FIG. 2, the arms 102 of the surgical instrument 100 are configured and adapted to triangulate with respect to one another. Each arm 102 includes a first segment 101 and a second segment 103 that are independently actuatable. Both the first and second segments 101, 103 include a plurality of rings 90. The rings 90 are axially aligned and are positioned adjacent to one another. The rings 90 are configured and adapted to interact with one another such that movement of one of the rings 90 results in a corresponding movement of adjacent rings 90.

Figure 3:
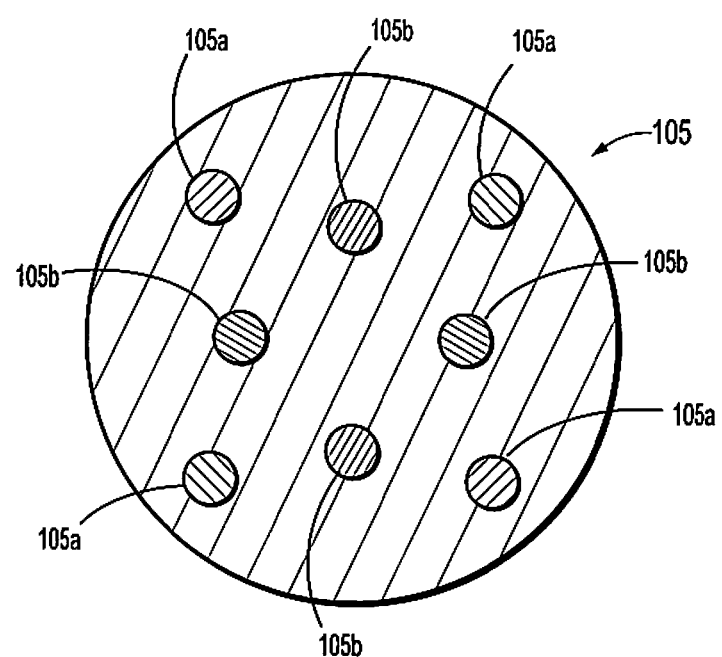
FIG. 3 is a cross-sectional view of the indicated area of the surgical instrument of FIG. 2.
Figure 4:
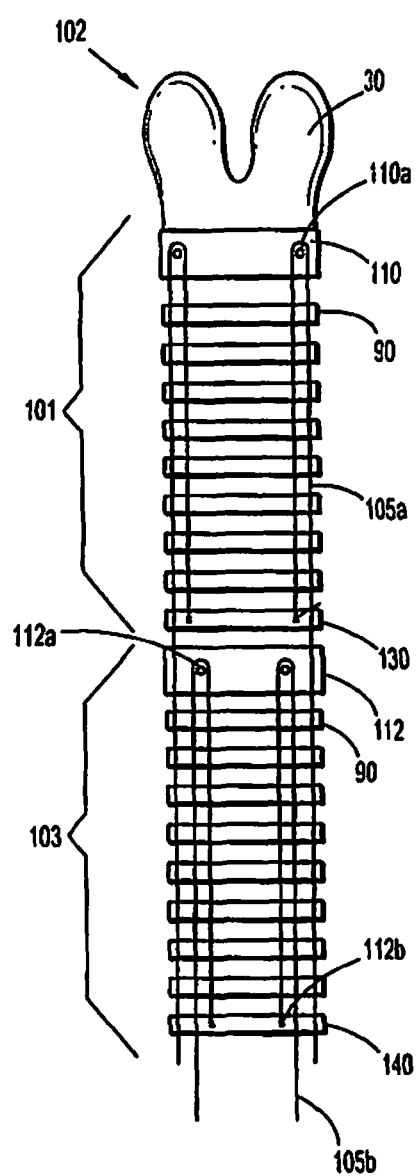
FIG. 4 is a schematic view of one of the arms of the surgical instrument of FIG. 2.

As shown best in FIG. 4, the first and second segments 101, 103 of the surgical instrument 100 are each actuated by cables 105 (FIG. 3). In particular, a first set of cables 105a controls movement of the first segment 101. Movement of the second segment 103 is controlled by a second set of cables 105b. As shown in FIG. 3, each of the first and second sets of cables 105a, 105b includes cables 105 that are arranged in pairs of generally opposing cables 105. By having cables 105 generally opposed from one another, movement of the segments 101, 103 (FIG. 2) may be caused in a first direction and in a second direction that is generally opposed from the first direction. Moreover, as shown in FIG. 3, the first set of cables 105a are radially grouped within the second set of cables 105b.

As shown in FIG. 4, each arm 102 includes a first end of each cable 105 of the first set of the cables 105a is secured to a first generally annular member 130 of first segment 101 and is looped through a channel 110a defined in a second annular ring 110. This looping of the cables 105 effectively doubles the strength of the cables 105. Each cable 105a of the first set of cables 105a passes through both the first and second segments 101, 103 of the surgical instrument 100. By applying a force to at least one of the cables 105a of the first set of cables 105a, the annular ring 110 is moved and causes a corresponding movement of adjacent rings 90. Similarly, a first end each cable 105b of the second set of cables 105b is fixed at one end to third annular ring 140 and passes through a channel 112a defined within a fourth annular ring 112. By applying a force to the second end of the each cable 105b of the second set of cables 105b, the fourth annular ring 112 is caused to move. The resultant movement of the fourth annular ring 112 causes the movement of the adjacent rings 90. As discussed above, each set of cables is independently actuatable and the movement of each segment 101, 103 of the arm 102 is independent.

Moreover, the arrangement and positioning of first and second sets cables 105a, 105b facilitates the independent actuation of first and second segments 101, 103. In particular, a force F1 may be applied to at least one of the cables 105 of the first set of cables 105a, while a different force F2 may be applied to at least one of the cables 105 of the second set of cables 105b.

Figure 5:
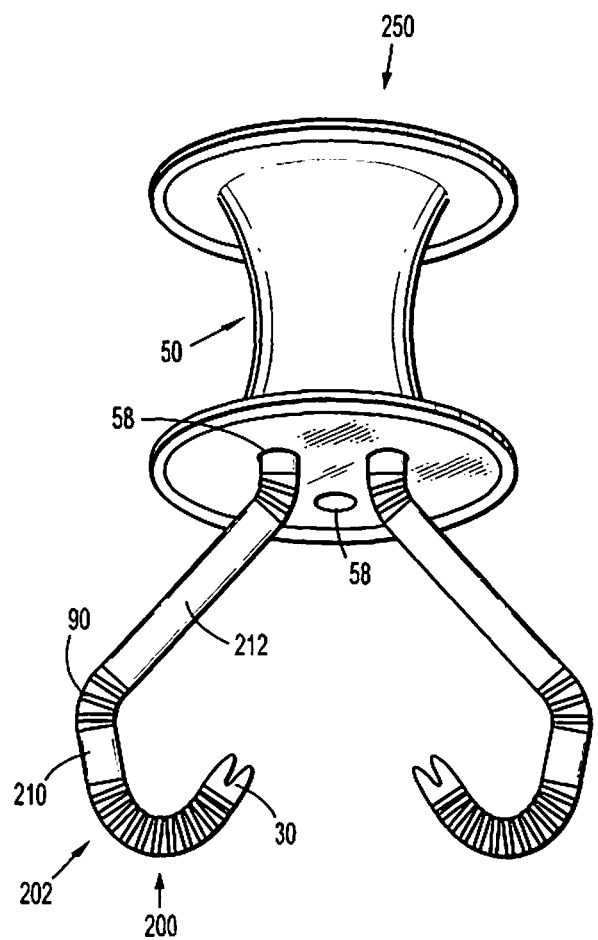
FIG. 5 is a bottom perspective view of a surgical system including a surgical instrument including arms in accordance with another embodiment of the present disclosure shown operatively coupled to the seal anchor member of FIG. 1.
Figures 6, 7:
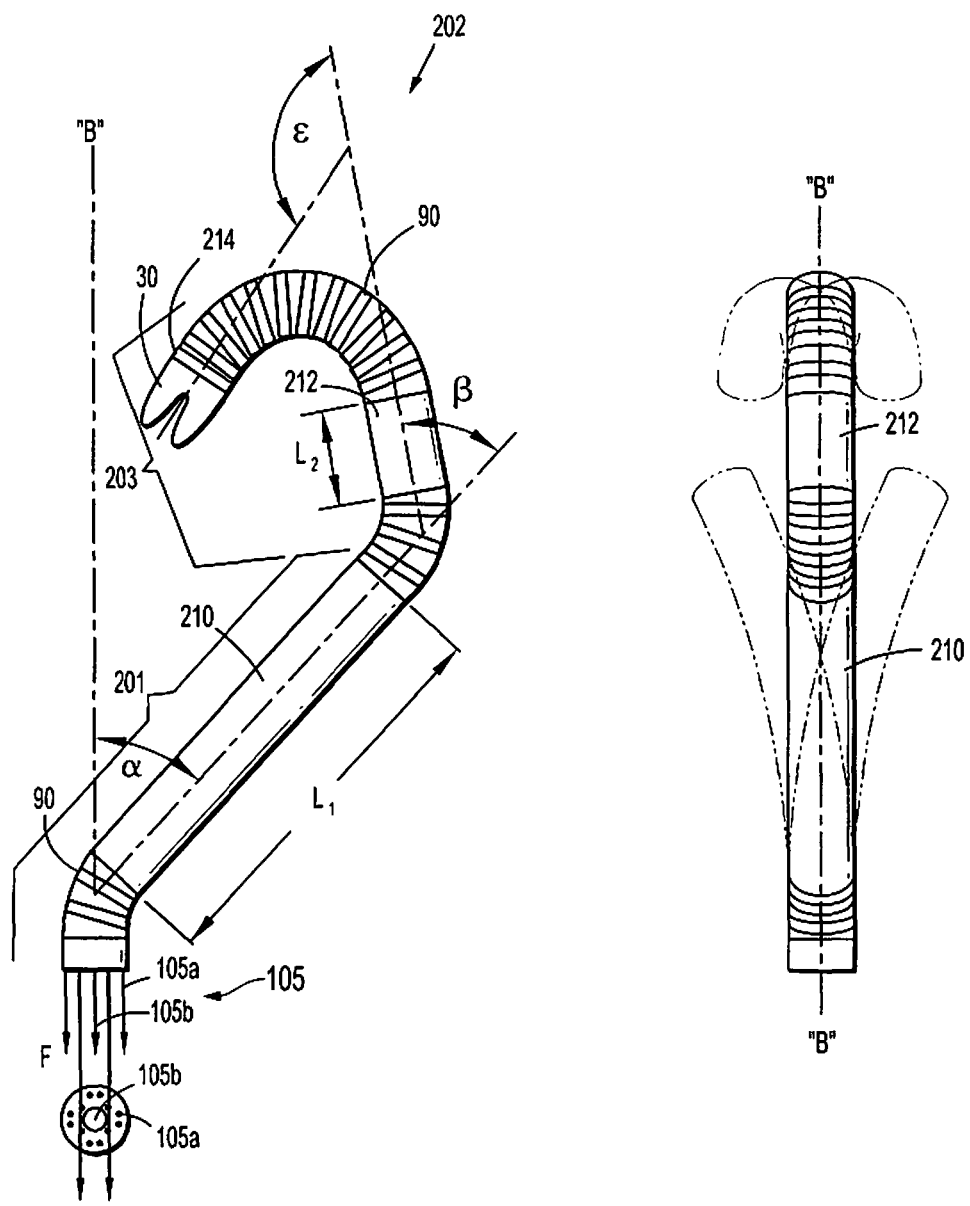
FIG. 6 is a perspective view of one of the arms of the surgical instrument of FIG. 5.
FIG. 7 is a perspective view of the surgical instrument of FIG. 6 illustrating in phantom alternative positioning of segments of the surgical instrument of FIG. 6.

With reference to FIGS. 5-7, a second embodiment of a surgical system including an instrument that is operatively coupled to a seal anchor member will now be described. A surgical system 250 includes a surgical instrument 200. The surgical instrument 200 is operatively coupled to the seal anchor member 50. The surgical instrument 200 is substantially similar to the surgical instrument 100, except in the following respects. In particular, the surgical instrument 200 includes a plurality of arms 202. As shown in FIG. 5, the arms 202 of surgical instrument 200 are configured and adapted to be placed within port 58 of the seal anchor member 50. Moreover, the arms 202 are configured and adapted to triangulate with respect to one another.

As shown best in FIGS. 6 and 7, each arm 202 includes a first segment 201 including a first annular member 210 and rings 90, and a second segment 203 including a second annular member 212. The annular members 210, 212 have different dimensions. In particular, the first annular member 210 has a longitudinal dimension $L_1$, and the second annular member 212 has a second longitudinal dimension $L_2$. Angular movement of each of the annular members 210, 212 effects a displacement of the portion of the surgical instrument 200 that is distal to each of the annular members 210, 212. In particular, the magnitude of the displacement of the distal ends of each annular member 210, 212 is a function of the relative change in the angle between the longitudinal axes of each annular member 210, 212 and the longitudinal axis "B". As shown in FIG. 6, each annular member 210, 212 may be angled from longitudinal axis "B" by an angle α, β, respectively. Moreover, the distal portion of the second segment 203 may be curved and angled by an angle ε with respect to the second annular member 212. In embodiments, the movement of the surgical instrument 200 may correspond to the dimensions of individual ring members 90. In addition, a pair of cables 105 extends to annular member 214 at the distal end of the surgical instrument 200 to effect positioning of the distal end.

Figure 8:
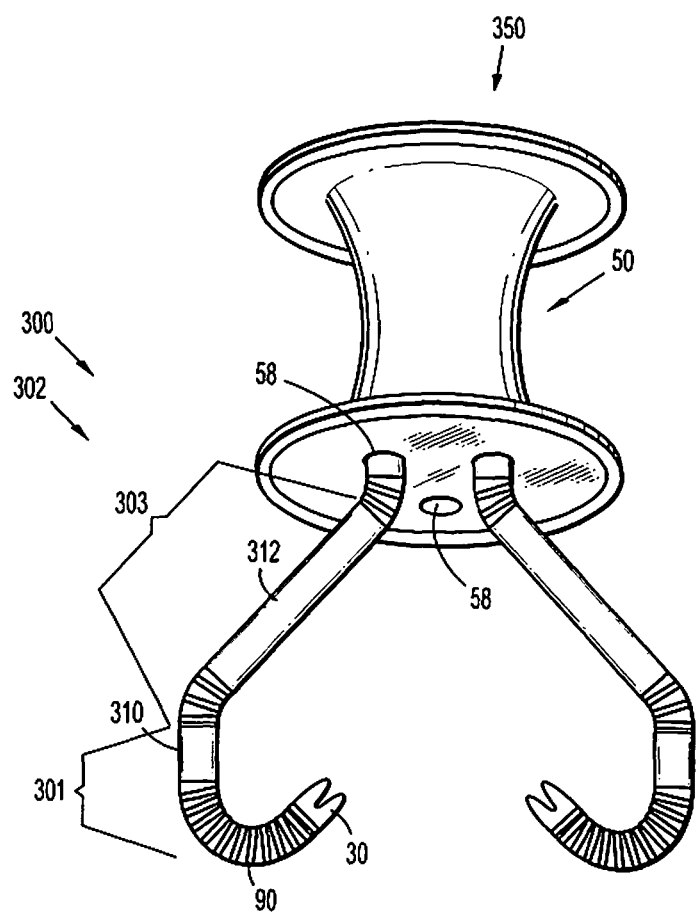
FIG. 8 is a bottom perspective view of a surgical system including a surgical instrument including arms in accordance with yet another embodiment of the present disclosure shown operatively coupled to the seal anchor member of FIG. 1.
Figure 9:
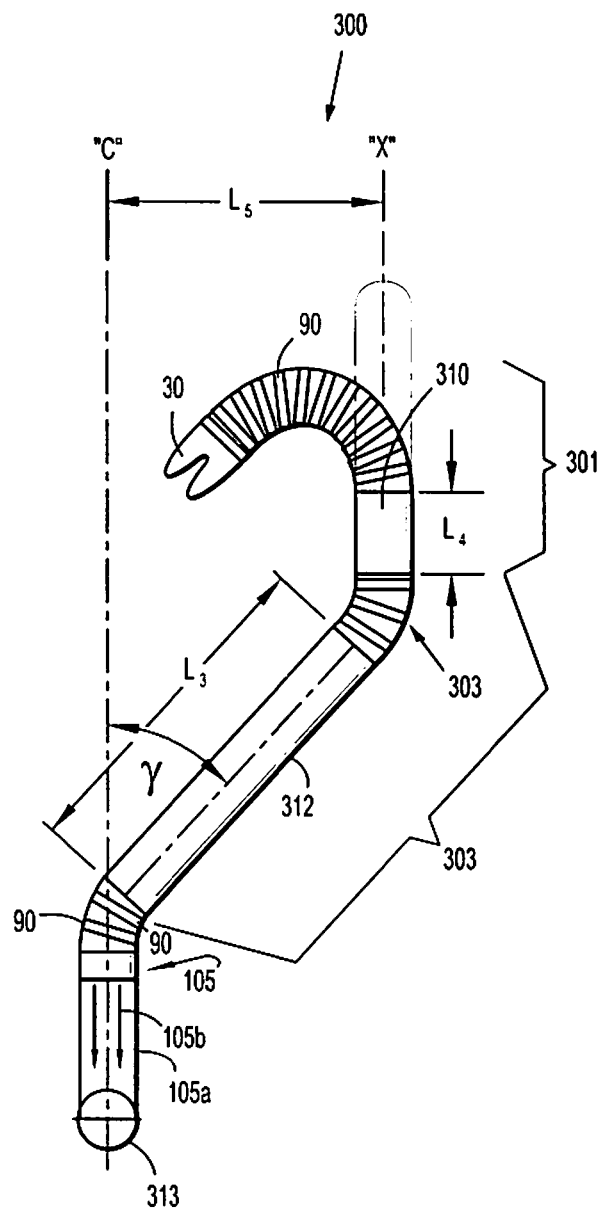
FIG. 9 is a perspective view of one of the arms of the surgical instrument of FIG. 8.

In a third embodiment, as shown in FIGS. 8 and 9, a surgical system 350 includes a surgical instrument 300. The surgical instrument 300 is operatively coupled to the seal anchor member 50. In particular, the surgical instrument 300 includes arms 302, each of which is configured and adapted to be placed within one of the ports 58 of the seal anchor member 50.

Each arm 302 of the surgical instrument 300 includes a first segment 301 and a second segment 302. The first segment 301 includes first annular member 310 and a plurality of rings 90. The distal portion of the first segment 301 may be angled with respect to the first annular member 310. The second segment 303 includes a second annular member 312 and a plurality of rings 90. This embodiment differs from surgical instrument 200 in the following ways.

As shown in FIG. 9, the first annular member 310 may have a length $L_4$ while the second annular member 312 has a length $L_3$. The first annular member 310 of the first segment 301 is configured and adapted to remain substantially parallel to longitudinal axis "C" as the second annular member 312 is radially translated by an angle γ, thereby axially translating the first annular member 310 by a distance $L_5$ from the longitudinal axis "C". In addition, a hub 313 is operatively coupled to the cables 105 such that the cables 105 form a closed loop. Rotation of the hub 313 causes movement of the cables 105 and a corresponding movement of the first and second segments 301, 302, as desired. As with the other embodiments, the cables 105 are divided into distinct sets 105a, 105b to cause independent actuation of the first and second segments 301, 302, respectively.

Figure 10:
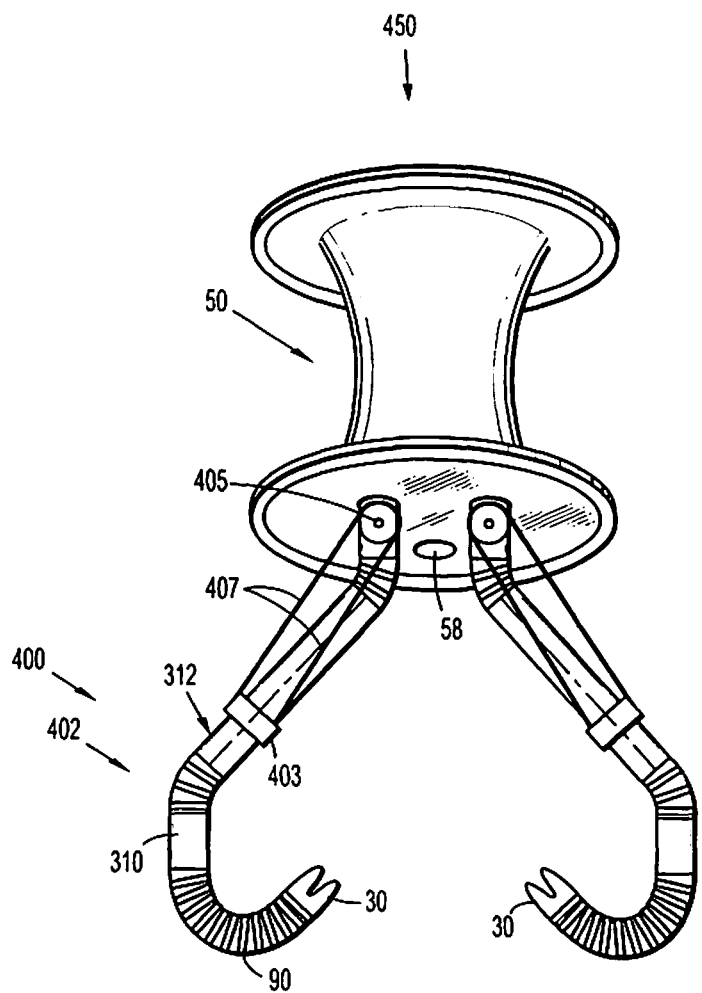
FIG. 10 is a bottom perspective view of a still further embodiment of a surgical system including a surgical instrument including arms in accordance with the present disclosure and shown operatively coupled to the seal anchor member of FIG. 1.
Figure 11:
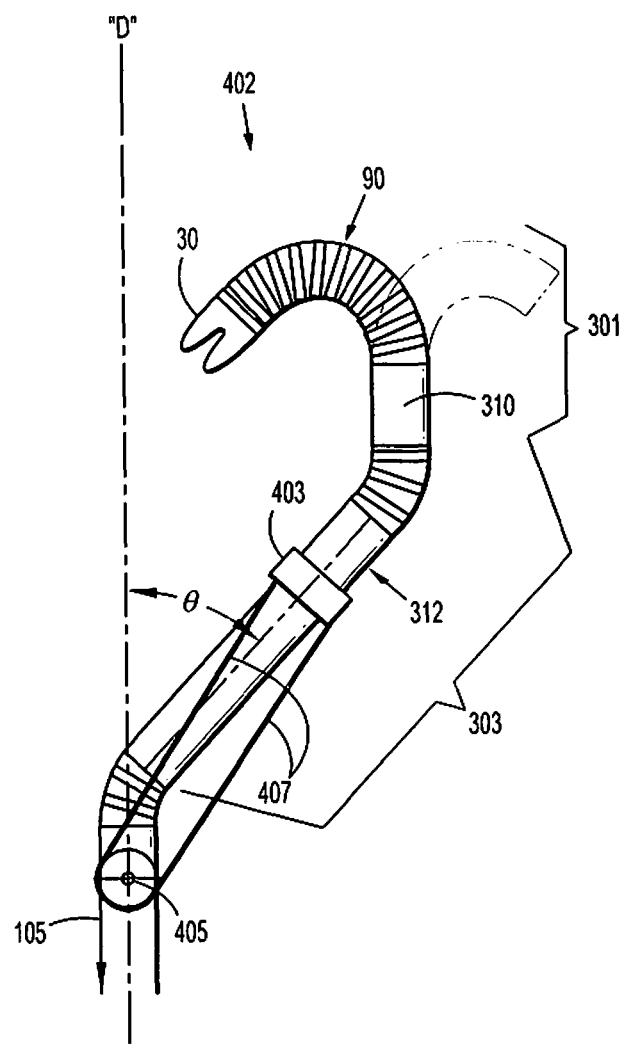
FIG. 11 is a perspective view of one of the arms of the surgical instrument of FIG. 10.

In a fourth embodiment, as shown in FIGS. 10 and 11, a surgical system 450 includes a surgical instrument 400. The surgical instrument 400 includes all the features of the surgical instrument 300 with the following differences that will now be discussed. The surgical instrument 400 includes a plurality of arms 402. The arms 402 are substantially similar to arms 302, but each also includes a collar member 403 that is disposed about the exterior of annular member 312 and axially translates along its longitudinal axis. Cables 407 operably couple the collar member 403 to a gear 405 to control the position of the collar member 403 along the annular member 312. The position of the collar member 403 along the annular member, as well as the tension exerted by the cables 407 on the collar member 403 that is disposed about the annular member 312, determines the position the annular member 312. In particular, the annular member 312 defines an angle θ with respect to longitudinal axis "D".

Figure 12:
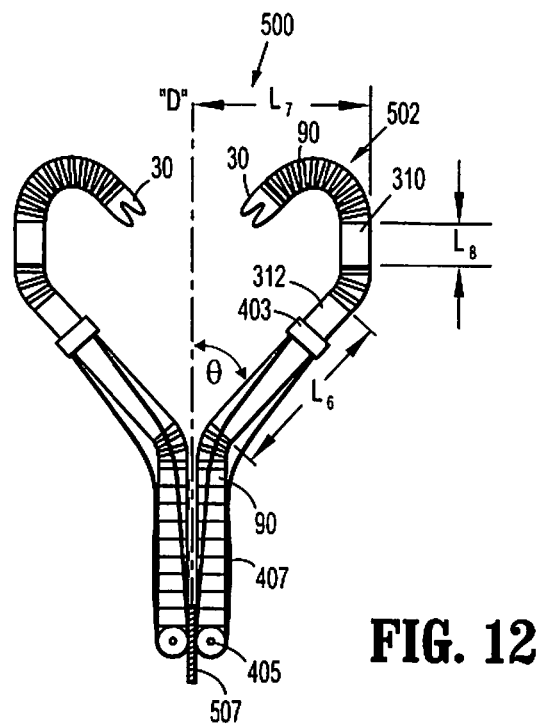
FIG. 12 is a perspective view of a yet a further embodiment of a surgical instrument in accordance with the present disclosure.
Figure 13:
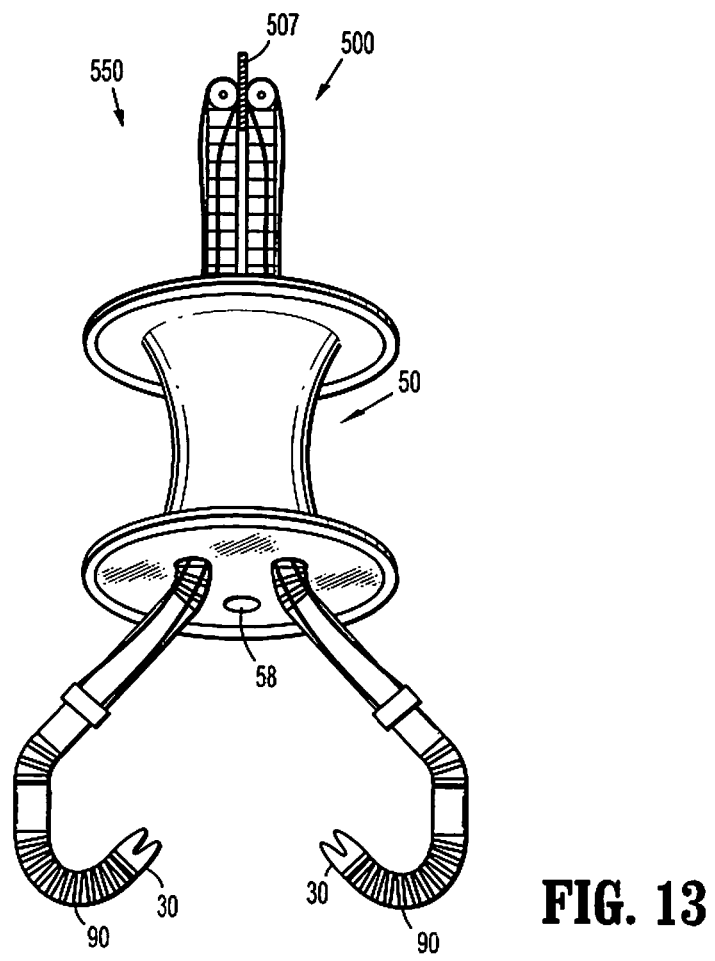
FIG. 13 is a bottom perspective view of a surgical system including the surgical instrument of FIG. 12 shown operatively coupled to the seal anchor member of FIG. 1.

In another embodiment, as shown in FIGS. 12-13, a surgical system 550 includes a surgical instrument 500. The surgical instrument 500 is operatively coupled to seal anchor member 50. The surgical instrument 500 includes all of the features of the surgical instrument 400, but differs in the following respects which will now be described. In particular, the surgical instrument 500 includes a worm gear 507 that causes rotation of the gear 405, thereby causes a corresponding translation of the cables 407 looped around gear 405 and the relative position of collar member 403 with respect to annular member 312. As the collar 403 is moved along the longitudinal axis of the annular member 312, the angle θ of the annular member 312 with respect to longitudinal axis "D" is determined.

Methods of using the surgical systems 150, 250, 350, 450, 550, which include surgical instruments 100-500, respectively, will now be described.

As described above and referencing FIG. 1, each of the surgical systems includes a seal anchor member 50. During a surgical procedure, the seal anchor member 50 is placed within tissue tract 12 that is defined between tissue surfaces 14 of tissue "T" in a substantially sealed relation therewith. The surgical instruments 100-500 may be coupled to the seal anchor member 50 prior to the insertion of the seal anchor member 50 within the tissue tract 12. Alternatively, the surgical instruments 100-500 may be operatively coupled to the seal anchor member subsequent to the placement of the seal anchor member 50 within the tissue tract 12.

With regard to surgical system 150 (FIG. 3), once both the seal anchor member 50 and the surgical instrument 100 are placed within the tissue tract 12, the arms 102 are movable such that the arms 102 can be triangulated with respect to one another. By individually moving first and second segments 101, 103 of the arms 102, the surgeon is able to triangulate the end effectors 30 of each arm 102 on a target location within the surgical site. In particular, as discussed above, each segment 101, 103 is individually actuatable by its own set of cables 105a, 105b, respectively. By actuating the sets of cables 105a, 105b of each arm 102, the position of the end effectors 30 with respect to each other and the target location can be controlled. In embodiments of the present disclosure, the arms 102 may move independently of one another or may move in a synchronized or choreographed fashion with respect to one another. In addition, the coordinates of the end effectors 30 may be determined to facilitate precise placement of the end effectors 30 with respect to the target location.

Regarding surgical system 250 (FIG. 5-7), the surgical system 250 is placed within the tissue tract 12 in a substantially similar manner as that described with respect to surgical system 150. As shown in FIG. 6, each segment 201, 203 of arms 202 can be articulated in opposite directions. In addition, the range of particular segments may be limited or restricted. The movement of the arms size of each of the segments 201, 203 is a function of the size of the segments 201, 203. Subsequent to the placement of the surgical system 250 within the tissue tract, the first segment 201 may be radially translated away from longitudinal axis "B", while the second segment 203 is radially translated in a direction toward the longitudinal axis "B". Each arm 202 may be independently actuated or may be actuated in a choreographed or synchronized fashion. As shown in FIG. 5, the end effectors 30 of arms 202 are triangulated with respect to one another. By triangulating the arms 202 with respect to one another, the end effectors 30 may be applied to a particular target location.

Use of the surgical system 350 (FIGS. 8-9) is similar in many respects to surgical system 250, with the following differences that will now be described. In particular, during use, the annular member 310 remains parallel relative to longitudinal axis "C". This allows for a single driving cable 105 in a closed loop to articulate each arm 302. In use, the articulation of the arm 302 may be caused by rotation of hub 313. As shown in FIG. 8, the arms 302 may be articulated with respect to one another to move the end effectors 30 in relation to one another. By knowing the initial position of the arms 302, and tracking the rotations of the hub 313, the position of arms 302 is ascertainable. In so doing, the end effectors 30 may be placed as desired on a particular target location.

The surgical system 450 (FIGS. 10-11) is placed within a tissue tract 12 in a substantially similar manner as described with respect to the other surgical systems. Once the surgical system 450 is placed within the tissue tract, the surgeon actuates arms 402 in a substantially similar manner as that described with respect to arms 302 of the surgical system 350 with the following differences that will now be described. In particular, the surgeon can also adjust the position of collar member 403 that is disposed about the exterior of annular member 312 of arm 402. During the procedure, the surgeon can apply a given force to cables 407 that are operably coupled to the collar member 403 of arm 402. In so doing, the angle θ between the annular member 312 and longitudinal axis "D" is adjustable.

The method and operation of surgical system 550 (FIGS. 12-13) is substantially similar to that described above with respect to surgical system 400 with the following differences. As already discussed, the surgical instrument 500 of surgical system 550 includes a worm gear 507 that causes rotation of the gear 405, thereby causing a corresponding translation of the cables 407 looped around gear 405 and the relative position of collar member 403 with respect to annular member 312. During use, the surgeon can rotate the worm gear 507 to cause a corresponding translation of the cables 407 looped around gear 405 and the relative position of collar member 403 with respect to annular member 312. In so doing, the surgeon moves the collar 403 along the longitudinal axis of the annular member 312, and determines the angle θ of the annular member 312 with respect to longitudinal axis "D".

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical system, comprising:
a seal anchor member including first and second longitudinally extending ports; and
a surgical instrument including a first arm and a second arm configured and adapted to be placed within the first and second longitudinally extending ports, respectively, each arm including:
a first segment including a plurality of rings and a first annular member disposed distal of the plurality of rings;
a second segment disposed proximal of the first segment, the second segment including a plurality of rings and a second annular member disposed distal of the plurality of rings of the second segment;
a first cable operatively associated with the first annular member of the first segment and having a first end secured to one of the plurality of rings of the first segment and a second end extending proximally from the first annular member;
a second cable operatively associated with the second annular member of the second segment and having a first end secured to one of the plurality of rings of the second segment and a second end extending proximally from the second annular member, wherein the first and second cables are independently actuatable, such that the first and second segments are independently actuatable.

2. The surgical system of claim 1, wherein the first and second annular members have different longitudinal dimensions.

3. The surgical system of claim 1, wherein the first and second annular members each have a longitudinal dimension and the displacement of a distal end of each annular member is proportional to the longitudinal dimension of each annular member.

4. The surgical system of claim 1, wherein the surgical instrument further includes a collar positioned about at least one of the first and second annular members, the collar repositionable along a longitudinal axis of the at least one of the first and second annular members, a position of the at least one of the first and second annular members corresponding to a position of the collar with respect to the longitudinal axis of the at least one of the first and second annular members.

5. The surgical system of claim 1, wherein the surgical instrument further includes a collar disposed about at least one of the first and second annular members, the collar translatable along a longitudinal axis of the at least one of the first and second annular members to cause movement of the at least one of the first and second annular members.

6. A method of performing surgery, comprising:
providing a surgical system including:
a seal anchor member including first and second longitudinally extending ports; and
a surgical instrument including a first arm and a second arm configured and adapted to be placed within the first and second longitudinally extending ports, respectively, each arm including:
a first segment including a plurality of rings and a first annular member disposed distal of the plurality of rings;
a second segment disposed proximal of the first segment, the second segment including a plurality of rings and a second annular member disposed distal of the plurality of rings of the second segment;
a first cable operatively associated with the first annular member of the first segment and having a first end secured to one of the plurality of rings of the first segment and a second end extending proximally from the first annular member;
a second cable operatively associated with the second annular member of the second segment and having a first end secured to one of the plurality of rings of the second segment and a second end extending proximally from the second annular member wherein the first and the second segments are independently actuatable; and an end effector on each of the first and the second arms; placing the surgical system within a tissue tract accessing an underlying surgical site;

actuating at least one of the first and second segments of at least one of the first and second arms to reposition the end effector of the at least one of the first and second arms;

engaging the end effector with a target tissue within the surgical site and performing a desired surgical procedure; and removing the surgical system from the tissue tract.

7. The method of performing surgery of claim 6, wherein the first and second annular members have d longitudinal dimensions.

8. The method of performing surgery of claim 6, wherein the first and second annular members each have a longitudinal dimension and the displacement of a distal end of each annular member is proportional to the longitudinal dimension of each annular member.

9. The method of performing surgery of claim 6, wherein the surgical instrument further includes a collar positioned about at least one of the first and second annular members, the collar repositionable along a longitudinal axis of the at least one of the first and second annular members, the position of the at least one of the first and second annular members corresponding to the position of the collar with respect to the longitudinal axis of the at least one of the first and second annular members.

10. The method of performing surgery of claim 6, wherein the surgical instrument further includes a collar disposed about at least one of the first and second annular members, the collar translatable along a longitudinal axis of the at least one of the first and second annular members to cause movement of the at least one of the first and second annular members.

11. The method of performing surgery of claim 6, wherein actuating at least one of the first and second segments of at least one of the first and second arms to reposition the end effector of the at least one of the first and second arms includes moving the end effectors of the first and second arms in a synchronized manner.

12. The method of performing surgery of claim 6, further comprising inserting the first and second arms through the first and second longitudinally extending ports, respectively.

13. The surgical system of claim 1, wherein the first annular member defines a channel which the first cable is looped.

14. The surgical system of claim 1, wherein the second annular member defines a channel which the second cable is looped.

15. The surgical system of claim 1, wherein at least one of the first and second arms includes a third cable opposing the first cable, the third cable operatively associated with the first annular member of the first segment and having a first end secured to the one of the plurality of rings of the first segment and a second end extending proximally form the first annular member.

16. The surgical system of claim 1, wherein at least one of the first and second arms includes a fourth cable opposing the second cable, the fourth cable operatively associated with the second annular member of the second segment and having a first end secured to the one of the plurality of rings of the second segment and a second end extending proximally form the second annular member.

* * * * *